United States Patent [19]

Riblet et al.

[11] 4,409,223

[45] Oct. 11, 1983

[54] ANXIOLYTIC METHOD

[76] Inventors: Leslie A. Riblet, 832 Walnut, Mt. Vernon, Ind. 47620; Michael S. Eison, 5487 Eden Dr., Evansville, both of Ind. 47715

[21] Appl. No.: 405,785

[22] Filed: Aug. 6, 1982

[51] Int. Cl.³ ............... A61K 31/495; A61K 31/505
[52] U.S. Cl. .................................... 424/251; 424/250
[58] Field of Search ............................... 424/250, 251

[56] References Cited

U.S. PATENT DOCUMENTS 3,717,634  2/1973  Wu et al. ........................ 424/250
3,907,801  9/1975  Wu et al. ........................ 424/250

OTHER PUBLICATIONS

K. L. Howard et al., J. Org. Chem., 18 p. 1484, (1953).
Carenini et al., Boll. Chem. Farm, 117 33–42, (1978).
Chem. Abst., 90:72148k, (1979).
Chem. Abst., 95:61854q, (1981).
Wu et al., J. of Medicinal Chemistry, 15/5, 477–479, (1972).

Primary Examiner—Stanley J. Friedman

[57] ABSTRACT

1-(2-Pyrimidinyl)piperazine and its pharmaceutically acceptable salts are useful in the alleviation of anxiety.

3 Claims, No Drawings

ANXIOLYTIC METHOD

FIELD OF THE INVENTION

This invention involves drug, bio-affecting, and body-treating compositions and methods employing a heterocyclic organic compound of the pyrimidine series as active ingredient (Class 424, Subclass 251).

BACKGROUND OF THE INVENTION

The chemical substance employed in the present invention was first synthesized by K. L. Howard, et al and reported in *J. Org. Chem.*, Vol. 18, page 1484 (1953). The authors found that 1-(2-pyrimidinyl)piperazine did not possess useful analgesic or antiparasitic (antifilarial) activity.

In much the same fashion, 1-(2-pyrimidinyl)piperazine has been used as a chemical intermediate for the synthesis of compounds with biological activity in a number of instances as borne out by the following representative references:

1. Carenini, et al., *Boll. Farm.*, 117, 33–42 (1978).
2. Khot, et al., *Chem. Abstr.*, 90:72148k, p. 514 (1979).
3. Indian Drugs and Pharmaceuticals, *Chem. Abstr.* (Pat. Abstr.) 95:61854q, p. 686 (1981).

Utility of this compound and related analogs as chemical intermediates in the synthesis of compounds with tranquilizing activity was disclosed in Wu, et al, U.S. Pat. No. 3,717,634 patented Feb. 20, 1973; U.S. Pat. No. 3,907,801 patented Sept. 23, 1975; and Wu, et al, *J. of Medicinal Chemistry*, 15/5, 477–479 (1972). Although 1-(2-pyrimidinyl)piperazine was subjected to in-house testing utilizing the same biological assays employed to determine tranquilizing activity for the claimed compounds in the Wu, et al patents, no activity of this sort was shown to be associated with 1-(2-pyrimidinyl)piperazine itself.

In summary, while 1-(2-pyrimidinyl)piperazine (MJ 13653) has been found to be useful as an intermediate in the preparation of biologically active molecules, nonetheless, no significant biological activity has previously been associated with the compound itself prior to the present invention.

SUMMARY OF THE INVENTION 1-(2-Pyrimidinyl)piperazine (I) has now been found to be useful as an antianxiety agent and is referred to hereinafter as MJ 13653. This compound has the following structural formula:

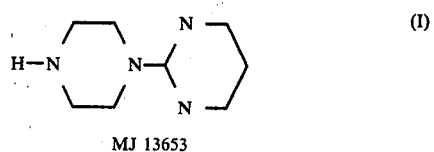

MJ 13653

DETAILED DESCRIPTION OF THE INVENTION

A number of laboratory methods have been developed for the measurement of the tranquilizing properties of a compound. Some of these pharmacological tests provide data which can differentiate between the antipsychotic and antianxiety components of biological action. Previous in-house testing of MJ 13653 indicated that the compound was inactive as a tranquilizer on the basis of suppression of conditioned avoidance response testing and radioreceptor binding assays. Conditioned avoidance response suppression testing in fasted rats treated orally with a test drug is a biological method which is indicative of anxiolytic and/or antipsychotic action without pronounced sedative effects. This method is adequately described in the Wu, et al, patents and publications cited hereinabove. Radioreceptor binding assays which measure the inhibition of binding of various neuronally active molecules are used to more specifically define tranquilizing activity. For example, inhibition of dopamine receptor binding indicates antipsychotic activity (Burt, Crease, and Snyder, *Molecular Pharmacology*, 12:800 (1976); Burt, Crease, and Snyder, *Science*, 196:326 (1977); Crease, Burt, and Snyder, *Science*, 192:481 (1976)). MJ 13653 was tested in a battery of receptor binding assays and was classified as inactive on the basis of established experimental criteria.

MJ 13653 was, however, retested using a laboratory method developed specifically for the measurement of antianxiety properties of a compound. This test method represents a modification of the Vogel Conflict test which is a simple and reliable conflict procedure for testing antianxiety agents (Vogel, Beer, and Clody, *Psychopharmacologia* (Berl.) 21, 1–7 (1971)). This test method is based on the finding that anxiolytics attenuate shock-induced suppression of feeding and drinking. In this test, water-deprived rats are given access to water bottles whose spouts are bracketed by a photocell, so that water ingestion (licks) can be quantified. After a predetermined number of licks, an electric shock is initiated across the cage-floor grid. The number of licks during non-shock and shock periods, the total number of shocks, and the cumulative latency to lick following shocks, are recorded. Analysis of these data are used to detect agents which will be of potential value as anxiolytic agents. This testing revealed that MJ 13653 possessed antianxiety properties, having a minimally effective oral dose of about 5 mg/kg.

Therefore, the main aspect of the instant invention concerns the process for ameliorating an anxiety state in a mammal in need of such treatment which comprises systemic administration to said mammal of an effective dose of about 0.1 to 40 mg per kg body weight of MJ 13653 or a pharmaceutically acceptable acid addition salt thereof. The term systemic administration as used herein refers to oral, rectal, and parenteral (i.e., intramuscular, intravenous, and subcutaneous) routes. Generally, it will be found that when MJ 13653 is administered orally, which is the preferred route; a larger quantity of the active agent is required to produce the same effect as a smaller quantity given parenterally. In accordance with good clinical practice, it is preferred to administer MJ 13653 at a concentration level that will produce effective anxiolytic effects without causing any harmful or untoward side effects.

The pharmaceutically acceptable acid addition salts are also considered useful as anxiolytic agents. By definition, these are those salts in which the anion does not contribute significantly to toxicity or pharmacological activity of the base form of MJ 13653. Acid additions salts are obtained either by reaction of MJ 13653 with an organic or inorganic acid, preferably by contact in solution, or by any of the standard methods detailed in the literature and available to any practitioner skilled in the art. Examples of useful organic acids are carboxylic acids such as maleic acid, acetic acid, tartaric acid, propionic acid, fumaric acid, isethionic acid, succinic acid, pamoic acid, and the like; useful inorganic acids are hydrohalide acids such as HCl, HBr, HI; sulfuric acid; phosphoric acid; and the like. It is also understood that since MJ 13653 has more than one basic nitrogen atom in its molecular structure, this allows MJ 13653 to form acid addition salts with the ratio of acid moiety to base being greater than one. The skilled practitioner appreciates that the exact ratio is a function of the stoichiometric amounts of acid employed and its relative acid strength.

Therapeutically, MJ 13653 is generally given as pharmaceutical composition comprised of an effective anxiolytic amount of MJ 13653 or one of its pharmaceutically acceptable acid addition salts and a pharmaceutically acceptable carrier. Pharmaceutical compositions which provide from about 1 to 500 mg of the active ingredient per unit dose are preferred and are conventionally prepared as tablets, lozenges, capsules, powders, aqueous or oily suspensions, syrups, elixirs and aqueous solutions.

Preferred oral compositions are in the form of tablets or capsules and may contain conventional excipients such as binding agents (e.g. syrup, acacia, gelatin, sorbitol, tragecanth, or polyvinyl pyrrolidone), fillers (e.g. lactose, sugar, maize-starch, calcium phosphate, sorbitol or glycine), lubricants (e.g. magnesium stearate, talc, polyethyleneglycol or silica), disintegrants (e.g. starch), and wetting agents (e.g. sodium lauryl sulfate). Solutions or suspension of MJ 13653 with conventional pharmaceutical vehicles are employed for parenteral compositions such as an aqueous solution for intravenous injection or an oily suspension for intramuscular injection. Such compositions having the desired clarity, stability and adaptability for parenteral use are obtained by dissolving from 0.1% to 10% by weight of the active ingredient (MJ 13653 or a pharmaceutically acceptable acid addition salt thereof) in water or a vehicle consisting of a polyhydric aliphatic alcohol such as glycerine, propylene glycol, and polyethylene glycols or mixtures thereof. The polyethylene glycols consist of a mixture of non-volatile, normally liquid, polyethylene glycols which are soluble in both water and organic liquids and which have molecular weights from about 200 to 1500.

DESCRIPTION OF SPECIFIC EMBODIMENTS

MJ 13653 may be synthesized according to methods readily available in the chemical literature, e.g. Howard, et al, *J. Org. Chem.* 18:1484 (1953). The following method of preparation is provided as a helpful example and is given for the purpose of illustration of a convenient synthetic method. Temperature are given in °Celsius.

Synthesis of MJ 13653

To a stirrred, warm (approximately 50°) solution of anhydrous piperazine (100 g, 1.16 mole) and sodium carbonate (58 g. 0.47 mole) in 465 mL of water was added 2-chloropyrimidine (53 g, 0.46 mole) in portions over about 1 hr. External cooling was required to maintain the temperature in the 50°–65° range. After the addition, the stirred reaction mixture was kept in the temperature range of 50°–65° for 1 hr and then allowed to slowly cool to 35° over a 2 hr period. The mixture was filtered, removing 1,4-dipyrimidinylpiperazine, and the filtrate was extracted with three 500 mL portions of chloroform. The chloroform extracts were dried (MgSO$_4$) and concentrated to 62 g (82%) of an oily solid which can be purified by distillation (bp, 118°–120°/2 mm) or converted to a salt form.

Conversion to the HCl Salt

Treating an ethanol solution of the base with an equivalent of ethanolic HCl yields the monohydrochloride salt. Recrystallization from ethanol yields white solid, m.p. 285°–287°, literature m.p. (Howard, et al) 289°–289.5°.

Anal. Calcd. for C$_8$H$_{12}$N$_4$.HCl: C, 47.89; H, 6.53; N, 27.93. Found: C, 48.05; H, 6.71; N, 28.09.

What is claimed is:

1. The process for ameliorating an anxiety state in a mammal in need of such treatment comprising systemic administration to said mammal of an effective but non-toxic anxiolytic dose of 1-(2-pyrimidinyl)piperazine or a pharmaceutically acceptable acid addition salt thereof.

2. The process of claim 1 wherein a pharmaceutical composition in unit dosage form suitable for systemic administration to a mammalian host is utilized which comprises a pharmaceutical carrier and an effective anxiolytic but non-toxic amount of 1-(2-pyrimidinyl)-piperazine or a pharmaceutically acceptable acid addition salt thereof.

3. The process of claim 2 wherein said pharmaceutical composition comprises an amount of 1-(2-pyrimidinyl)piperazine to provide an effective anxiolytic but non-toxic dose of from 0.1 to 40 mg/kg body weight of said host.

* * * * *